United States Patent [19]

Relihan

[11] 4,454,606

[45] Jun. 12, 1984

[54] RECONFIGURABLE X-RAY AEC COMPENSATION

[75] Inventor: Gary F. Relihan, Nashotah, Wis.

[73] Assignee: General Electric Company, Schenectady, N.Y.

[21] Appl. No.: 497,098

[22] Filed: May 23, 1983

[51] Int. Cl.³ .......................... A61B 6/00; H05G 1/44
[52] U.S. Cl. ...................................... 378/97; 364/414; 378/108
[58] Field of Search ................... 378/97, 108; 364/414

[56] References Cited

U.S. PATENT DOCUMENTS 4,158,138  6/1979  Hellstrom .............................. 378/97

FOREIGN PATENT DOCUMENTS 143692  9/1980  German Democratic Rep. .. 378/108

Primary Examiner—Alfred E. Smith
Assistant Examiner—T. N. Grigsby
Attorney, Agent, or Firm—Fuller, House & Hohenfeldt

[57] ABSTRACT

An automatic x-ray exposure time control wherein compensation curves representative of plots and reference signal voltages versus integrated x-ray dose signals can be reconfigured to account for the variable effects on x-ray film density resulting from the specific image receptor, collimator field area, x-ray intensity sensor and density factor used in any x-ray exposure technique over a range of operator-selected x-ray tube kilovoltage (kV) and current (mA). Data for a relatively small number of basic compensation curves are obtained and stored in ROMs. These curves are plots of exposure times versus integrated x-ray dose signals which resulted in producing a constant predetermined and desired film density for whatever amount of x-ray attenuating material is in the x-ray beam. Each basic curve is obtained with the x-ray tube operating at a particular kV and mA. Gain factors are developed in accordance with the respective image receptor, x-ray sensor, collimator setting and density factor used during an actual patient exposure. A basic compensation curve is called up in response to the user selecting a tube kV and mA. The ordinates of the basic curve are multiplied by the gain factors. The results are acted on by an algorithm that yields a corrected compensation curve and the data are put in a memory device in the form of binary representations of reference voltages versus exposure times. During an exposure the reference voltages are clocked out in time sequence and compared with the integrated dosage signal. When a comparison is made, the exposure is caused to terminate.

10 Claims, 3 Drawing Figures

RECONFIGURABLE X-RAY AEC COMPENSATION

BACKGROUND OF THE INVENTION

The invention disclosed herein relates to automatic control of the duration of x-ray exposures for assuring that an x-ray image recorded on a medium such as film will have proper density.

Many systems for accomplishing automatic exposure control (AEC) have been devised. Generally, the operator is required to select an x-ray tube current value and an x-ray tube anode applied kilovoltage (kV) value that will produce an x-radiation beam having, respectively, corresponding x-ray photon intensities and energies for producing an image of the anatomy that will have the desired density for maximizing diagnostic information and for comfortable viewing. A device is provided in the system for developing a reference signal that is adjustable to take into account several variables which are present in the system. A signal from a sensor or detector, that senses the optical radiation or x-radiation dose during an exposure, is integrated. A comparator device usually compares the increasing integrated signal continuously during the exposure with the reference signal. When the two signals become matched or equal, corresponding to proper film density having been obtained, the comparator trips and produces a signal that is used to terminate the exposure by deenergizing the x-ray tube.

Obtaining good exposure timing accuracy over the full range of exposure times has been problematical. Modern AEC systems are capable of terminating long duration x-ray exposures quite accurately so as to produce acceptable film density. However, when short duration exposures such as 20 milliseconds (ms) or less are made, certain variables in the system are likely to bring about exposure timing errors which are a greater percentage of the total optimum exposure time. Hence, film densities can vary appreciably between different x-ray technics.

Variables that introduce errors in timing are such things as contactor delays which may result in the x-ray tube becoming energized somewhat after the exposure start signal is given and to become deenergized somewhat after the signal for terminating the exposure has been developed. Optimum timing may vary nonlinearly over a range of selected x-ray tube current milliamperages (mA). The charging capacitance of the high voltage cables that lead from the x-ray power supply to the x-ray tube may affect the rise time and fall time of the x-ray beam pulse. The optical or x-radiation detector or sensor may have non-linear sensitivity relative to x-ray photon energy during the exposure, or, in other words, to the kilovoltage (kV) applied to the x-ray tube. The detector response or rise and fall time may have one form for one detector and another form for another detector. Different types of radiation intensity detectors may be used for different procedures. For instance, an ion chamber may be used as the detector for radiographic procedures wherein the x-ray image is recorded directly on film in a cassette. A photomultiplier (PM) detector may be used where light is piped to it from the output phosphor of an x-ray image intensifier such as is the case when photospot film recording is in progress. X-ray image intensifiers have a rise and decay time and are also sensitive to x-ray tube kV or photon energy as manifested by a varying transfer function. At least in radiography, it is not only use of films that have different film speeds that may differ from one procedure to another, but the intensifying screens interfaced with the film may also have different properties such as different rise and decay times, different sensitivities to different x-ray energies or tube kV. In addition, a collimator is usually used to define the boundaries of the x-ray beam and the collimator open area is likely to be different for imaging different anatomical regions. Furthermore, the operator can select the film density desired for best visualizing the details of the anatomical region of interest by selecting an x-ray tube kV and current or mA which experience or charts show produce a predetermined film density.

Attempts have been made to compensate AEC systems for the foregoing and other variables and to provide compensation that is unique to any given x-ray procedure or set of exposure factors. The approach is to store data representative of the curves for compensating a timing interval for almost any combination of variables. One approach has been to determine the minimum number of compensation curves required for a definite number of procedures so as to minimize the numbers of them that have to be stored. Typically the data representative of the curves has been stored in individual look-up tables that are applicable to a number of procedures. Experience has shown that as many as 72 integrated circuit look-up tables are required to handle most of the combinations of variables that exist and must be accounted for in different x-ray procedures.

SUMMARY OF THE INVENTION

An object of the invention is to provide an automatic exposure control system that maintains its timing accuracy and, hence, film density control over a wide exposure time range.

Another important object is to provide for developing the data for an exposure compensation curve substantially concurrently with the operator choosing the x-ray tube kilovoltage and current factors. An important adjunct to this object is to require only one compensation curve temporary storage device that is loaded concurrently with selection of the x-ray tube exposure factors.

Another very important object and feature of the invention is that it permits adding or substituting components such as radiation detectors, film and intensifier screen combinations and image receptors that cooperate with the integrated radiation and reference signal comparison circuitry of an AEC system without having to make any changes in the AEC circuitry. This result is achieved by letting the influence exerted by any of said components or other components on the desired exposure time be represented by a gain factor. Hence, when a component is added or substituted it is only necessary to determine its gain factor and use this gain factor along with gain factors associated with components in the system already to modify any of the stored basic timing compensation curves.

How the foregoing and other more specific objects of the invention are achieved will appear in the more detailed description of a preferred embodiment of the invention which will now be described in reference to the drawings.

DESCRIPTION OF A PREFERRED EMBODIMENT

Figure 1:
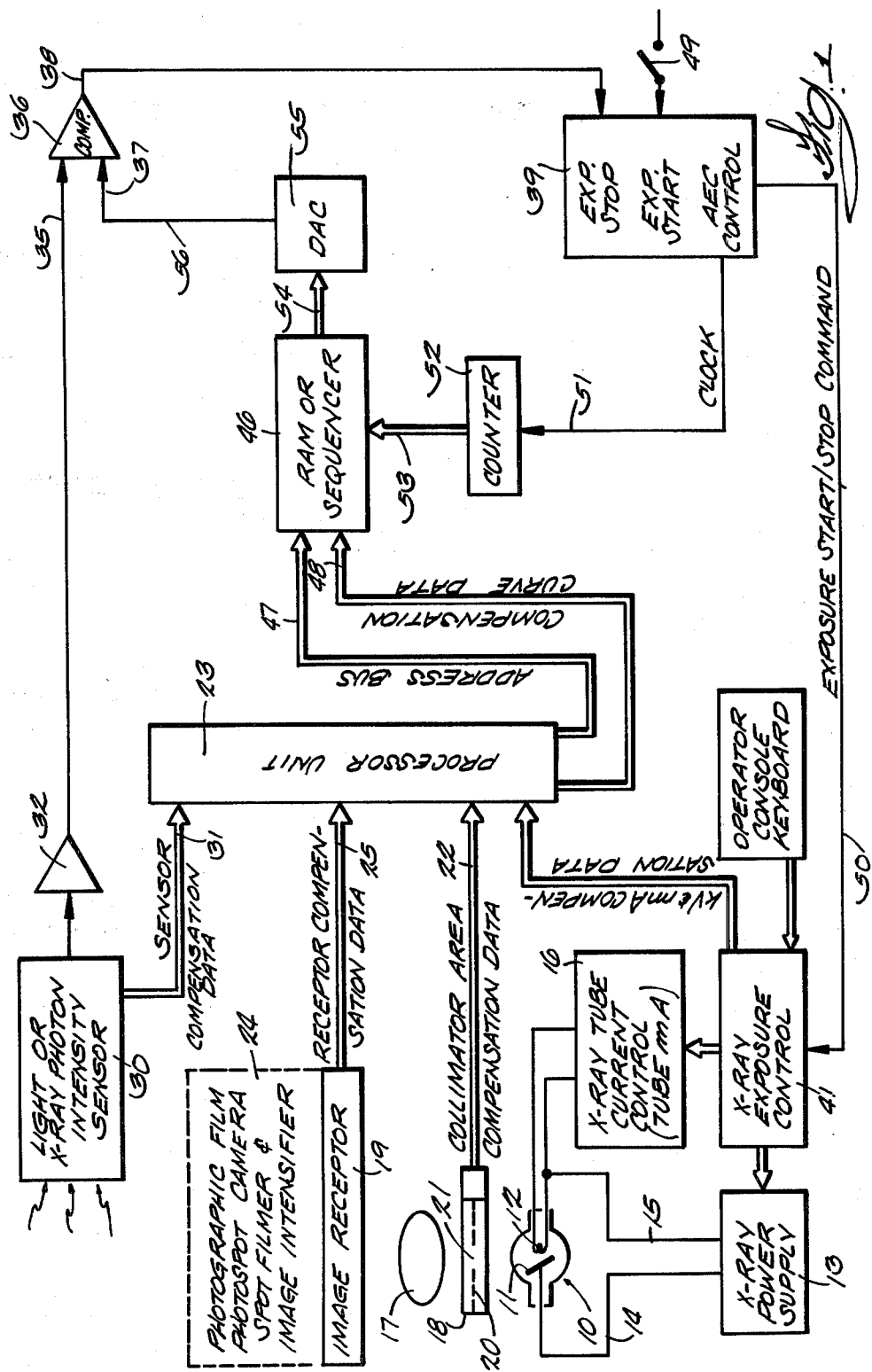
FIG. 1 is a block diagram of a diagnostic x-ray system in which the new automatic exposure control device is incorporated.

Referring to FIG. 1, some of the components in a conventional diagnostic x-ray system will be outlined first and then the new automatic exposure control (AEC) or phototiming device will be described. In the left region of FIG. 1, an x-ray tube 10 is shown. Its anode or target is identified by the numeral 11. The x-ray tube contains the usual electron emissive filament or cathode 12. The electron beam focusing cup that is usually associated with the cathode has been omitted. In any event, when a positive kilovoltage is applied to anode 11 and the filament is heated, the electron beam impinges at a focal spot on anode 11 and produces an x-ray beam emanating from the focal spot.

The x-ray power supply is symbolized by the block marked 13. Two of the conductors 14 and 15 by which the high voltage is applied between x-ray tube anode 11 and cathode 12 are usually formed in a cable insulated with a material that has high dielectric strength. As is known, the cable must necessarily be quite long so it has small but significant capacitance. The x-ray power supply also contributes to the capacitance of the high voltage system. Hence, as is known, when a square wave high kilovoltage x-ray tube anode energizing pulse is applied across conductors 13 and 14 charging the cable capacitance and other capacitance and other capacitance will result in increasing the rise time of the pulse. When the high kilovoltage is removed at the end of the pulse to terminate the x-ray exposure, discharge of the cable capacitive current results in the applied kilovoltage decaying with some delay instead of decaying or falling instantaneously. The retarded rise time and extended decay time cause little percentage error in the exposure interval when the interval is long such as well over 20 milliseconds (ms). However, for short duration x-ray exposures such as below 20 ms or less the rise and decay times represent a substantial percentage of the exposure interval and, hence, a great variation in the density on the image recording medium. The effect of capacitance in the x-ray tube power supply circuit is one of the effects which the new automatic exposure control system described herein is designed to compensate.

The contents of the x-ray power supply block 13 are not shown but it will be understood to contain a conventional step-up transformer for developing the high kilovoltage that is applied between the anode 11 and cathode 12 of the x-ray tube 10. The secondary of the transformer supplies a full-wave rectifier so that dc may be applied between the x-ray tube anode and cathode. An autotransformer in the step-up transformer primary circuit permits setting the ac voltage that is applied to the primary winding of the step-up transformer and, hence, the kilovoltage output level of the secondary winding of the step-up transformer. It is assumed in this case that to start an x-ray exposure a switch will be closed in the autotransformer and step-up transformer primary circuit and that the switch will be opened to terminate the exposure. Silicon controlled rectifiers are usually used as the switching elements in the x-ray power supply primary circuit. Electromagnetic contactors or relay switches are also frequently used. Either type of switch opens or closes in response to occurrence of a gate or other control signal that is intended to either start or stop an x-ray exposure. SCRs may not reach peak conductivity for one-tenth of a millisecond after receiving an exposure start gate signal. Electromagnetic contactors may act even slower. This is a significant delay if the exposure interval is only one or a few ms long. The new AEC control described herein also provides compensating for variations in contactor operating time from system to system.

As is known, the energy or penetrating power of the x-ray photons generated by the x-ray tube is proportional to the kilovoltage that is applied between the anode 11 and cathode 12 of the x-ray tube. The quantity or intensity of the x-ray photons is proportional to the electron beam current that flows between the anode 11 and cathode 12 of the x-ray tube. The beam current level is governed by operating the cathode filament 12 in an emission-limited mode. That is, for any filament current the filament will attain a maximum temperature and, hence, a rather definite emissivity. X-ray tube current is an exposure factor that is chosen by the operator. The x-ray tube current control is symbolized by the block marked 16. It can be looked upon as being conventional in that it contains a step-down transformer and some means such as a tap switch in the primary circuit which will allow for establishing a wide variety of secondary voltages and currents that are applied to the filament of the x-ray tube.

X-ray tube kV and mA are selected by the operator before an exposure. The selected levels of an x-ray tube current or photon intensity and applied kilovoltage or x-ray energy do not directly affect nor require compensation insofar as exposure time is concerned but other elements such as the x-ray intensity sensors in the system may have different sensitivities at different x-ray tube applied kilovoltages and rise and fall times of kilovoltage will vary with tube current levels so these latter factors must be taken into account in connection with compensating for variables in other parts of the system.

In FIG. 1, a patient undergoing x-ray examination is represented by an ellipse marked 17. The x-ray beam emitted from x-ray tube anode 11 is defined by a collimator represented by the block marked 18. The x-ray image resulting from the differentially attenuated x-ray beam passing through patient 17 may be received by one of several types of image receptors which are designated generally by the block that is so labelled and further identified by the reference numeral 19.

Collimator 18 is conventional in that is comprises a housing containing pairs of orthogonally movable blades 20 that define an opening or x-ray beam cross-sectional configuration 21. The collimator blades are typically driven by a servo motor, not shown. Means, not shown, are provided for producing signals indicative of the size of the opening between the collimator blades and, hence, the x-ray beam field size. These signals may be conducted by way of a bus 22 to a processor or control unit represented by the block marked 23. The signals are representative of gain factors and will be discussed later. Since the collimator field size may differ for different x-ray exposures it is necessary to compensate for variable field size in order to get an image of proper density in the x-ray film or other image receptor element. The new AEC system compensates for this variable too.

Automatic exposure control may be used for timing exposures where different types of image receptors are used. Some of the receptors which may be present in an x-ray system are listed in the dashed line rectangle 25 which is appended to the image receptor block 19. An x-ray image intensifier is one of the listed receptors. The image intensifier may be the well known type wherein the x-ray image falls on an image phosphor layer that converts the x-ray image to light of proportional intensity. The light image excites a photoemissive layer and the emitted electrons are focused on an output phosphor which converts the electron image to an optical image which may be recorded on film while using automatic exposure duration control to obtain the proper film density. Compensation must be made for the fact that image intensifiers and other receptors may have different sensitivities for different x-ray tube applied kilovoltages or photon intensities that may be used in various x-ray procedures.

Another image receptor indicated in rectangle 24 is a spot filmer which is conventional. As is well known, a spot filmer or spot film device is often used with an image intensifier. The conventional spot filmer comprises a carriage that shifts a film cassette in the x-ray beam to expose or form an image on selected areas of the film. Generally, the spot film cassette is projected into the x-ray beam path to make a permanent recording of an image or series of images that have been previously visualized on an image intensifier. Here again, film speed and the variable dynamic characteristics of any film such as the non-linear relationship between x-ray intensity and film density or darkening over a range of x-ray photon intensities and energies must be taken into account and compensated for. The new AEC system described herein affords this type of compensation too.

In many x-ray diagnostic systems a photospot camera as is listed in rectangle 24 is optically coupled to the output phosphor of the image intensifier for permitting obtaining a rather rapid sequence of photographs of the optically converted x-ray image. Here again, automatic exposure control is usually used.

Another receptor listed in rectangle 24 is radiographic film which is usually in a light tight cassette during an x-ray exposure. The cassette is arranged in the x-ray beam emerging from the patient and allows making a permanent recording of an image on film. Radiographic film cassettes invariably contain an intensifying screen that emits light when subjected to differentially attenuated x-ray photons and the light augments exposure or excitation of the film. Intensifying screens also have different characteristics or variables which must be accounted for or compensated for in addition to compensating for the type of radiographic film that is being used in the radiographic film cassette.

It will be evident that different types and degrees of compensation will be required for each of the image receptors just discussed in order to get accurate AEC timing intervals that will produce recorded images having the optimum density for providing maximum diagnostic information. In any case, the receptor compensation data (essentially a gain factor as will be discussed later) will be introduced into control unit 23 by means of a bus 25 which simply symbolizes that these data are provided for compensation.

In an automatic exposure control x-ray procedure the operator chooses two of the x-ray tube factors, namely, the kilovoltage that is to be applied to the x-ray tube anode during an exposure interval and the x-ray tube current. Means are usually provided for allowing the operator to obtain the film density in accordance with his or her preference. The x-ray tube kilovoltage (kV) and current (mA) and the desired film density are independent variables whereas the exposure time required to produce a film having the desired density is a dependent variable. Thus, in an automatic exposure control procedure, the radiation dose must be integrated or measured in a cummulative fashion in order to determine when the exposure should be terminated to obtain the desired film density. Moreover, some means must be provided to sense the x-ray intensity continuously during the exposure interval and means must be provided for integrating a signal corresponding to x-ray dose rate so that when a predetermined dose level is reached the exposure will automatically terminate. Optical (light) or x-ray photon intensity sensors may be used. Block 30 in FIG. 1 symbolizes various sensors. In some cases, such as when the image receptor is radiographic film, the conventional practice is to use an ion chamber, not shown, for detecting or sensing accumulated x-ray dose during an exposure interval. As is known, the ion chamber may be interposed in the x-ray beam path between the x-ray source and radiographic film for the purpose of producing an electric current that is proportional to the ionizing effect of the x-radiation. An ion chamber may also be used for measuring dose rate during spot filming. When a photospot camera is in use, a fiberoptics bundle is sometimes aimed at the output phosphor of the image intensifier. The light is conducted by the bundle to a photodetector such as a phototransistor which produces a current signal that is proportional to the intensity or brightness of the output phosphor. Thus, in general, a means is required for producing an electric signal that is proportional to instantaneous light or x-radiation intensity and the signal must be integrated until it compares in magnitude with a reference signal. When a comparison is made, a signal is produced which brings about termination of the exposure. Radiation sensors and integrators are so well known to those familiar with AEC that further elaboration should not be necessary. It should be understood, however, that any versatile diagnostic system wherein various kinds of image receptors are used will employ different kinds of x-ray dose rate sensors and each will have its own peculiar characteristics. For example, sensor sensitivity usually is variable with or a function of x-ray tube kV or photon energy. In FIG. 1, the bus 31 symbolizes that signals indicative of the sensor that is being used are provided to processor 23 for use in connection with determining a gain factor that is used in the process of developing compensation curve data that is required to govern the exposure time for any given set of system variables such as image receptor sensitivity, collimator area, sensor sensitivity, x-ray tube kV and mA.

In FIG. 1, the integrated dose rate signal produced by the light or x-ray intensity sensor is supplied to a gain adjustable amplifier and ramp generator combination represented by triangular block 32. Two typical linear ramp signals for different x-ray techniques are marked 33 and 34 in FIG. 2 which will be discussed in greater detail later. For the time being it is sufficient to recognize that the magnitude or level of the integrated or ramp signal is a function of time and relates to x-ray dose rate.

Referring to FIG. 1 again, during an x-ray exposure the ramp signal is fed to one input 35 or an operational amplifier which is connected for operating in a comparator mode and, in the illustrated embodiment, comparator 36 compares analog signals. The other input 37 to comparator 36 is for introducing a reference signal with which the ramp signal on input 35 is compared. The manner in which the reference signal is generated is a significant feature of the invention discussed herein. When a comparison is made, comparator 36 changes the state on its output signal terminal 38 and this signal is conducted to an AEC control unit 39 which is effective to bring about termination of the exposure assuming one has been started previously. In accordance with the invention, it is the signal to input 37 of comparator 36 which is adjusted in a unique fashion to bring about termination of any exposure at a time that takes into account or compensates for all of the previously discussed component variables which may differ depending upon whether a radiographic filming, photospot filming or spot filming procedure is being used. It will be evident to those skilled in the art that a large number of compensation curves would have to be generated to cope with all possible combinations of image receptors, collimator areas, focal spot-to-film distances and x-ray tube kV and mA. Previously, the compensation curve data were generated for a limited number of exposure factor combinations. These data were typically stored in read-only memory (ROM) chips. Typically, the data for 40 to 60 compensation curves were stored in a corresponding number of ROMs. The ROM data that brought about the closest compensation was automatically chosen after the operator selected x-ray tube kV and mA and desired film density. Thus, compensation for any given set of exposure factors was in a sense, a compromise. To provide compensation for every conceivable combination of exposure factors and variables in the system thousands of stored compensation curves would be required. In accordance with the invention, only data representative of the characteristics of the various sensors, image receptors and collimator areas need be generated to modify one of a small number of basic compensation curves required for any given exposure. The merit of this is that only one memory is required for holding the modified or corrected final compensation curve during any given exposure.

Before describing how the basic and final or modified compensation curve signal is generated and supplied to one input 37 of comparator 36, it may be noted in FIGURE 1 that the user interface with the system is through an operator console keyboard which is symbolized by the block marked 40. The user presses keys on the keyboard or operates independent switches, not shown, to select the desired x-ray tube kV and mA and desired film density. Other keys are pressed to indicate the type of image receptor that will be used for the particular exposure. Collimator cross-sectional area is also adjusted by pressing keys on the console keyboard 40. In any event, the encoded information thus produced is supplied by way of bus 9 to processor unit 23 before the x-ray exposure is initiated.

A block marked 41 contains the components such as the electronic or electromagnetic relay switch devices for turning the x-ray tube on and off.

Figure 2:
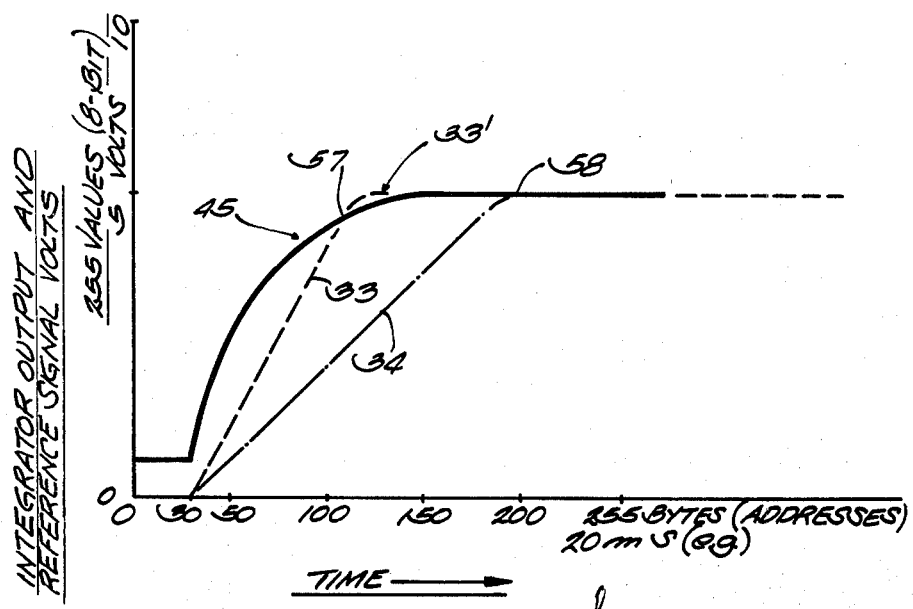
FIG. 2 is a typical exposure compensation curve that will be referred to in connection with explaining the invention.

The manner in which the basic and final compensation curves are generated will be described in detail later. The plot of an illustrative final compensation curve 45 is shown in FIG. 2. One should note now that the basic compensation curve data, which is modified to produce the final curve data, is stored in ROMs in the processor 23 for example. The final or corrected compensation curve data which is generated when kV and mA are chosen is stored for any given exposure in some electronic storage device from which it can be accessed in real time such as a random access memory (RAM) or sequencer represented by the block marked 46 in FIG. 1.

Assume, for the sake of example, that storage device 46 is a RAM. Now referring to FIG. 2, one may note that in an actual embodiment, by way of example and not limitation, the RAM has 256 addressable bytes ranging from 0 to 255 and represented along the abscissa of the graph in FIG. 2. Each byte corresponds to an increment of exposure time expressed in milliseconds as is also denoted along the abscissa. Thus, in this particular example, 20 ms of exposure time is divided into 255 parts or locations each of which is addressable. Looking at the ordinate of the plot in FIG. 2, one may see that each byte has a depth of 8 bits so that the compensation curve 45 signal magnitude can range from 0 to 255 values. In this particular case where number values are used for the sake of clarity that results from using typical numbers from an actual embodiment, the 8 bits or maximum of 255 represents the total of 10 volts so the orginate of the graph is also labelled with this voltage. The reason that curve 45 can become substantially horizontal or linear after a certain amount of exposure time has elapsed is that the variables such as differences in sensor sensitivities and in the dynamic characteristics of the films and due to the x-ray tube cable and power supply capacitance cause exposure timing errors that are of little consequence for exposure intervals beyond a certain length.

Consider now that the data for a particular compensation curve 45 has been generated in control unit and processor 23 prior to initiation of an x-ray exposure. Before the exposure starts, the final or corrected compensation curve data are loaded into RAM 46. The 255 abscissa or time bytes in FIG. 2 are RAM addresses. The RAM is addressed for loading by way of address bus 47 in FIG. 1. The ordinates or compensation curve values correspond to reference voltages and are sent to the addressable locations in the order to the addresses by way of compensation curve data transfer bus 48. Now assume the phototimed exposure is started by closing manual switch 49 leading to AEC control block 39. This results in an exposure start command being sent from AEC control 39 by way of a line 50 to the x-ray exposure control circuitry 41. The x-ray exposure control 41 causes the x-ray tube to become energized to initiate the exposure which, of course, may have to be 1, 2 or 3 milliseconds long on some occasions or much more than 20 ms long on other occasions in order to get proper film density.

During an exposure, RAM 46 is read out at a clocked rate. This is, compensation curve reference voltages relative to exposure times are read out. AEC control 39 contains the clock pulse generator which is not shown. The clock pulses are supplied by way of a line 51 to a digital counter represented by the block marked 52. The counter outputs digital values 0 to 255 in succession in response to counting the clock pulses. These output values on a bus 53 are addresses to RAM 46 so it outputs the ordinates or signal values for curve 45 on the RAM output bus 54. The digital values on bus 54 are converted to corresponding analog signal values by means of a digital-to-analog converter (DAC) represented by the block marked 55. The continuous analog voltage signal is fed by way of a line 56 to the reference signal input 37 of comparator 36 as previously mentioned. For the sake of example, consider that the readout of RAM 46 began at the time of about address 30 in FIG. 2 as this is the time that the sensed or integrated x-ray photon or light intensity signal represented by ramp 33 in FIG. 2 began to appear at input 35 of comparator 36. In other words, the ramp signal is rising with time depending on the actual intensity or total dosage of the radiation that is being sensed. The illustrative ramps are shown to start about 1.2 ms after the exposure start command is given due to x-ray power supply contactor delay, for example.

In any event, as can be seen in FIG. 2, when the integrated ramp voltage signal 33 attains the same value as the compensation curve 45 as has occurred at intersection point 57 in FIG. 2 for example, comparator 36 and its output changes state to thereby deliver an exposure stop signal by way of line 38 to AEC control 39. This signal is transmitted by way of the exposure stop command line 50 to the x-ray exposure control module 41 which brings about deenergization of the x-ray tube. The signal to stop x-radiation occurred at point 57. However, the sensor and, hence, the image receptor may receive a little more radiation due to persistence of the image intensifier and delay due to x-ray power supply opening time delay as indicated by the ramp extension beyond point 57 and marked 33'.

Assume now that part of the anatomy is moved into the x-ray beam path which anatomy has greater thickness and, hence, higher x-ray attenuation than the anatomy which was exposed and resulted in a ramp having the slope of ramp signal 33 in FIG. 2. In a case where x-ray attenuation is high, a ramp such as that represented by the dashed line 34 in FIG. 2 might be produced. Naturally the higher attenuation would result in a greater time being required to produce the desired film density. This is the case with ramp 34 which intersects with the compensation curve and causes tripping of comparator 36 to terminate the x-ray exposure and the referenced and sensed ramp voltage compare as at point 58 in FIG. 2. Note that there is no need to compensate beyond the time at which point 58 occurs or even before it since timing errors due to contactor opening time delay and image intensifier screen persistence are an insignificantly small percentage of total exposure time.

As stated earlier the final or corrected basic compensation curve that is required for compensating the exposure time for a contemplated x-ray exposure at any operator-selected x-ray tube anode kV and tube current or mA is developed immediately after the mA and kV have been selected and before the exposure start command is given. The final compensation curve data for any set of x-ray tube mA and kV are based on modifying one of a set of basic compensation curves that are in storage and are obtained by means which will be explained below. In other words, digital data for a final compensation curve will be developed for every exposure that is a modification of a selected one of the basic curves. The shape of the final compensation curve depends on the system variables that are in effect during any x-ray technique. For instance, chosing to operate in the spot filming, photospot or radiographic filming mode may result in the basic curve related to a particular mA and kV combination being modified differently than for another kV and mA combination. In the radiographic mode, for example, how one of the basic compensation curves is modified will depend on the radiographic film and intensifying screen combination that is used. In some x-ray systems by way of example, ten different film and screen combinations may be used whereas in others there may be only five to content with. Each film and screen combination is likely to have a different sensitivity or response to the same amount of radiation. The basic compensation curve that is applicable to any selected mA and kV selection will also have to be modified in accordance with the type of radiation sensor that is used.

The set of basic compensation curves must be provided and stored to account for the timing errors that can result from the characterisitics of the x-ray tube power supply. These errors are significant during short AEC exposures such as exposures under 20 ms duration. As previously indicated, timing errors due to delayed closing of the contactor in the x-ray power supply circuit after the exposure start command is given and delayed opening after the exposure stop signal is given are rather constant at any selected x-ray tube kV and mA but they must be accounted for. Inherent capacitance in the x-ray tube power supply, including the cables that supply the x-ray tube, can cause variations in the rise and fall times of the x-ray pulse depending on the selected kV and mA levels. For instance, with a fixed inherent capacitance it will take longer to discharge the cables when a high mA has been flowing before the contactor opens than when low mA has been flowing so the pulse has a longer decay time and the exposure is extended. When longer exposures are determined by the AEC, such as above 20 ms, rise and decay time and other timing errors due to the power supply have little significance because the errors are such a small percentage of the whole timing interval.

In accordance with the invention, a set of basic compensation curves for selected combinations of kV and mA over a range of 60 to 150 kV and 10 to 1000 mA are typically required. On first impression this appears to be a high number and would require a lot of ROM storage as compared to the prior art approach where an attempt was made to get by with one curve. But one curve was usually nothing more than a poor compromise and compensation could not be made substantially independent of the x-ray power supply characteristics nor did it permit taking into account how the curve should be modified when different radiation sensors, film-screen combinations, imaging modes and so forth were involved in an AEC system.

The basic compensation curves are plots (actually data representative of coordinates) of the reference voltage that must be produced at any given exposure time to get a film image having proper density. Basic curves are obtained as follows. The x-ray power supply, switching devices or contactors, x-ray tube, x-ray tube supply cables and so forth that are to be controlled by the AEC system are used to get the data for the basic curves. A conventional pre-existing AEC system may be used with this equipment and this implies that a sensor senses the radiation during an exposure, the sensor signal is integrated to indicate dose rate, the integrated signal is compared with a reference signal and when the signals reach equality a command signal results which effects turning off the x-ray tube to end an exposure.

The first operation prior to developing one of the basic compensation curves is to calibrate the AEC system which may be a prior art system that has an integrator and comparator comparable to integrator 32 and comparator 35 and that terminates the x-ray exposure when a comparison is made.

To calibrate, put a multiple layer x-ray attenuating phantom in the x-ray beam. Select the lowest kV that will be applied to the x-ray tube in the design range, such as 60 kV and an intermediate mA, that is, x-ray tube current to obtain a permitted dose level and use enough phantom to assure that when an exposure is made it will terminate automatically at above 20 ms, such as at 40 ms, where power supply variables have no effect. Develop the exposed x-ray film and check if it has a desirable density. Adjust the gain of the amplifier-integrator such as the one marked 32 in FIG. 1 up or down depending on whether the film was not dense enough or too dense. This step may have to be repeated to obtain the desired reference density and corresponding base voltage on the integrator 32 output. Now the system is calibrated at the desired x-ray dose level. Record the base voltage produced by the integrator. Assume, for example, that this voltage is 5 volts in a range of 0 to 10 volts. This voltage corresponds to calibrated and desired film density that one will want to obtain at any chosen kV and mA within limits for any thickness of the phantom and, hence, any corresponding patient thickness.

Figure 3:
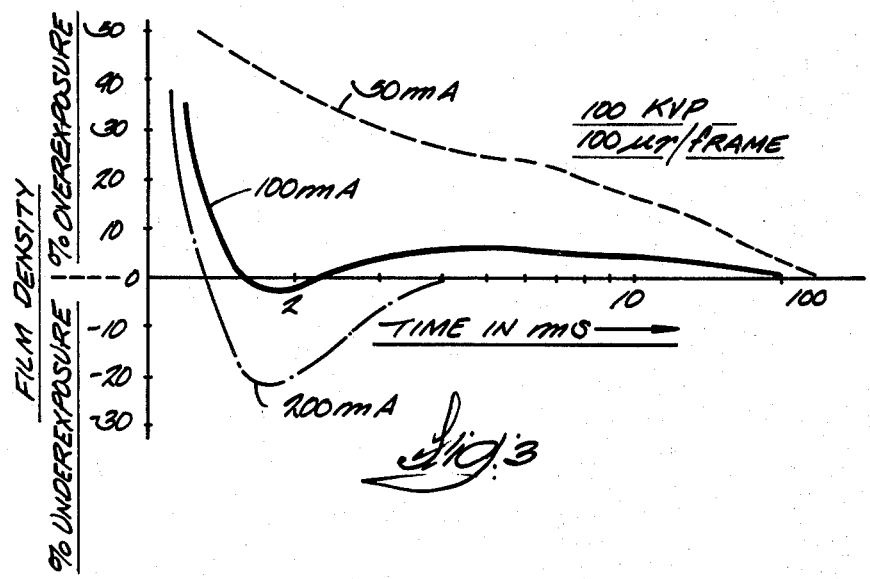
FIG. 3 is a set of curves for exposures made at a fixed x-ray tube applied voltage and three different x-ray tube current values to show how overexposures and underexposures can result when the only variable between exposures is the change in thickness of the phantom or body being exposed in a conventional or prior art AEC system.

Now to develop the first basic compensation curve data set, an estimation must be made as to the values of the voltages that are to be supplied to the reference voltage input 37 of comparator 36 while the base or integrator voltage to input 35 is held constant and while exposures are made at constant selected x-ray tube applied kV and mA but with stepwise decreases in phantom thicknesses. In a sense, one needs a plot of reference voltage levels versus exposure times to get the same integrated dose or film density for any phantom thickness step. A plot or curve of this type can be considered a first order or first approximation compensation curve. It is based on prior experience with AEC systems and is likely to be predictable with some errors because timing errors in AEC systems are not consistent. By way of example, consider the curves or plots in FIG. 3 of film density versus various x-ray tube currents and a constant applied kV obtained while using a prior art compromised compensation curve. Emergent radiation from the phantom was 100 microroentgens ($\mu r$) per frame. Note that at low x-ray tube current, that is, at 50 mA there was about 40% overexposure where the exposure terminated in about 2 ms and about 10% overexposure or excessive film density with a thicker phantom in the beam where exposure terminated in about 80 ms. The other two illustrative curves obtained with 100 mA and 200 mA x-ray tube currents show that both overexposures and underexposures can occur with the same mA and kV as phantom or patient thickness changes. Also note that as exposure times increase to where variable timing errors have a smaller percentage effect on total exposure time, film density gets closer to the desired value.

Return to the matter of developing first approximation and then basic compensation curves. For the first trial and after system calibration as described above has been done, a low x-ray tube kV and mA is selected, as an example and not to imply a limitation, assume 60 kV and 10 mA. From prior knowledge it is determined that at this kV and mA and with a specific phantom thickness in the beam an exposure should terminate in a roughly known number of milliseconds. A reference voltage for input to comparator input 37 is estimated, based on prior experience data for this exposure. Likewise reference voltages are selected which are believed to be close to those required to match the integrated voltage signal supplied to comparator input 35 after calibration. What is being done is empirical development of the data for a first approximation compensation curve representing exposure time in terms of reference voltages versus film density in terms of integrator signal amplitude.

Then the exposure sequence is started with a particular phantom thickness, preferably great enough thickness to have a comparison be made between integrator signal and reference signal at slightly more than the 20 ms critical point used for demonstration herein. An oscilloscope or other instrument is used to measure the time in milliseconds when tripping of comparator 36 occurred to terminate the exposure and the time is recorded. The integrator output voltage reached at the time a comparison was made with the estimated reference voltage fed to comparator input 37 is recorded. If the integrator voltage was above the base voltage of 5 volts it means a film would be overexposed and if below the base a film would be underexposed. So the thing to do is lower or raise the reference voltage and repeat the exposure at 60 kV and 10 mA with the same phantom thickness in the beam. Assume for example on the first pass the integrator signal reached 6 volts before tripping which would indicate overexposure of a film. In such case one would reduce the reference voltage by a small amount and make another exposure at the same kV, mA and phantom thickness. The exposure would, of course, terminate in a shorter time than the preceding one. This step may have to be repeated until a reference voltage is established that results in causing the comparator to trip so that the integrator reached 5 volts and the predetermined film density would have been obtained. The reference voltage and the time in milliseconds for the exposure to terminate is recorded. This provides for one data point on a basic compensation curve which, in the last analysis, is a plot of reverence voltage values versus exposure times.

Now to get the other points on the first basic compensation curve, one increment of phantom thickness is removed and the process of modifying the reference voltage in this example until exposure at the same kV and mA terminates at 5 volts on the integrator is repeated. The exposure time and reference voltage are recorded. Now the phantom thickness is reduced step-by-step down to the least attenuation expected by a patient and for each step the preceding procedure is repeated to get enough data points to produce a reasonably good plot without having to get a reference voltage point for every millisecond as yet. Generally, getting 14 to 20 points for a curve is sufficient but, of course, the curve will be stepped and not smoothly curved. As will be discussed later a computer algorithm is used to develop a more nearly smooth curve. This will result in 20 ms of exposure time on the abscissa of the curve plot embracing the critical range wherein compensation is necessary. As will be elaborated later, the exposure time over the range of up to 20 ms in this example is digitized and each ms or fraction thereof is represented by a byte whose value corresponds to a particular time.

Now the whole cycle is repeated to get another basic compensation curve of integrator voltage versus exposure time. This time the kV would be at 60 kV again but a new mA of rather arbitrarily about 20% larger or possibly 10 or 15 mA larger would be used. On this cycle or pass the reference voltages required could be more quickly determined by starting with the reference voltages found to be appropriate in the first cycle. Another compensation curve would be thereby developed and it is likely that its data would actually or nearly coincide with the first cycle data. In any event, the measuring cycles would be repeated for additional mA steps at the same kV up to the mA limit ever expected to be used on a patient. This will result in collecting dozens of preliminary basic compensation curves.

In addition to the foregoing cycles, preliminary compensation curves data are generated for different kV levels wherein kV is held constant and measurements are made over the full range of mA values used in the first cycle. Typically, the highest kV level would be about 150 kV. This would result in data for dozens more of preliminary basic compensation curves.

However, it will become evident that several curves or sets of data obtained in consecutive order such as with a constant kV and a range of x-ray tube mAs will differ from each other only slightly and that an intermediate or average one of the curves can be chosen as representative of a range of mA values at a particular kV so the number of final basic compensation curves is reduced drastically. Thus, in accordance with the invention, when the operator selects a kV value and an mA value appropriate to a contemplated x-ray procedure, the basic compensation curve for that kV and for a range of mA values embracing the selected mA value will be called up. The data, of course, for each basic compensation curve will be stored in a separate ROM area and will be subject to being modified as required to account for effects on exposure times resulting from variables introduced by such as the collimator area, film speed, intensifier screen characterisitics and radiation intensity sensing device selected for use in the procedure.

Typically there may be 20 to 40 points or x,y coordinates of time and integrator voltage, respectively, on a preliminary basic compensation curve and about the same number on a compromise curve or curve that resulted from combining similar curves that can be used for compensating over a limited range of selected kV and mA values without significant loss of compensation. This is especially so because a relatively small density change, under 25% for example, can hardly be detected by one viewing the radiograph. So the combined compensation curves are still coarse straight line approximations which must be smoothed in order to be able to divide the curve, at least up to the end of the first 20 ms of exposure time, into smaller time intervals of 100 microseconds or less.

Assume now that the basic compensation curves have been smoothed and the computer printout provides the x coordinates, representing exposure times in milliseconds, and the y coordinates, representing integrator signal magnitudes. The x,y coordinates representing each basic compensation curve are digitized and formed into tables which are stored in read only memories (ROMs) that, for the sake of simplifying the drawing, can be considered to be situated in processor unit 23 in FIG. 1. If these curves were plotted they would be shaped generally similarly to the one illustrative final or ultimate compensation curve 45 in FIG. 2 but they would be stepped and not smooth as shown. Which one of the basic compensation curves will be used and modified for an x-ray exposure depends on the kV and mA selected by the operator for the exposure. Thus, it will be evident that timing errors that would otherwise be introduced by the x-ray power supply and switching time and capacitance caused variances are negated already because the basic curves properly relate exposure time and integrator signal magnitude for the kV and mA selected. So there is no variable due to the x-ray tube power supply characteristics.

But further compensation is needed for any exposure to account for the effect on x-ray dose that results from the particular collimator area that is to be used, and for the different sensitivities of the various radiation intensity detectors to the x-ray tube applied kV, and for different combinations of x-ray film types and intensifying screen types, and for the various film density factors that the operator may select.

As indicated early in this specification in reference to FIG. 1 further compensation correction data are supplied to the processor unit 23 from the radiation sensor unit by way of bus 31, from the image receptor by way of bus 25, from the collimator by way of bus 22 and the kV and mA date and the operator selected film density factor by way of bus 9. These dates are expressed in terms of gains. $G_A$ is the normalized gain factor for collimator 21 area compensation. $G_K$ is the normalized gain factor for radiation detector 24 sensitivity to kV. $G_S$ is the normalized gain factor for film and intensifier screen combination sensitivities. $G_D$ is the selectable density factor. These gain factors can be encoded. For instance, the collimator puts out a gain factor signal, $G_A$, proportional to the area of the opening between the collimator blades by, for example, using a potentiometer, not shown, to generate the signal in response to blade position. Film and intensifying screen combinations gains $G_S$ are developed in response to coding on the film cassette. Similarly gain signals, $G_S$, are developed in dependance on whether the photospot camera or spot filmer is in use. $G_K$ is also predetermined and represented by an encoded signal that depends on the radiation intensity sensor that is used.

By way of example, for $G_K$ which accounts for sensor sensitivity, one may select a sensor used in the system as typical and assign to it a gain of 1 when an arbitrary x-ray tube applied voltage of 80 kV is used and calibrate the integrator amplifier 32 at this kV. Then one may add or subtract gain for different sensors.

$G_A$ is assigned a value of 1 when full open collimator area is used. Any reduced collimator area used during an exposure would be a fraction lower than 1.

$G_S$, for the film/intensifying screen combination, is determined by making exposures with all combinations expected to be used. Additional gains, $G_S$, must be determined for spot film and photospot procedures. In any case, exposures are made with a known kV on the x-ray tube, such as 80 kV, and the integrator-amplifier gain is adjusted until exposures yield the proper film density. The changes in gain of the integrator-amplifier is then indicative of the change in gain required for the respective filming technique. These $G_S$ gain factors can be stored and called up in response to the operator inputting a request for any of the techniques by using the console keyboard 40.

$G_D$, gain for desired film density is a linear gain that affects the amplitude of the basic mA and kV compensation curve that is in use.

Now assume that the basic compensation curve data sets are stored in ROM. As previously indicated, each curve or plot of exposure time versus integrator voltage will be formed with 14 to 25 x,y coordinate points so little ROM capacity is required for the basic compensation curves. The gain factors also are now accessible when the parameters for an exposure are set. An exposure is ready to be made and the ultimate or final compensation curve data for a curve such as in FIG. 2 is to be developed and stored in RAM 46. As can be seen in FIG. 2 the critical exposure interval of about 20 ms in this embodiment is apportioned to 255 bytes in RAM. Each byte corresponds to approximately 80 microseconds. The byte numbers are addresses to the RAM locations that store the integrator 32 output voltage values where in this example the 5 volts that cause the comparator 36 to trip and stop the exposure. These data are stored in RAM as 255 8-bit words representing 0 to 10 volts and they are ordinates for tne curve. In other words, RAM 46 will perform as a look-up table during the exposure interval. The basic curves will be reconfigured in accordance with the gain factors pertaining to the exposure.

The objective is to provide a table containing the coordinates required to form a final compensation curve for the given input data. These coordinates are used to form a straight line approximation of the required final compensation curve by applying the Bresenham straight-line algorithm with the aid of processor unit 23. The algorithm is frequently used by those skilled in the art and is described in an article: J. E. Bresenham, "Algorithm for Computer Control of a Digital Plotter," *IBM Systems Journal*, Vol. 4, No. 1, 1965, p. 25. Definitions:

A. f(a,y)=final compensation curve
  a=amplitude (0-255 bytes on the ordinate)
  b=time increment (0-255 bytes on the abscissa)
  "y"=represents and address location in RAM 46
  "a"=represents a byte value at "t" address.
b. $(x_1,y_1)(x_2,y_2) \ldots (x_n, y_n)$ are the data consisting of amplitude (y) and time increment (x) defining a compensation curve based on operator selected x-ray tube kV and mA.

By applying the following equation to each set of coordinate points the table of coordinate points is developed and stored in RAM and it will provide proper compensation for the total system:

$$a_i = G_A \cdot G_K \cdot G_S \cdot G_D \cdot x_i \text{ where } x_i = 1 \ldots n$$

The gains are multiplied together and used to multiply each ordinate or "y" value corresponding to the respective "x" coordinate values 1 ... n. This yields:

$$f(a,y) = (a_1y_1),(a_2y_2), \ldots (a_ny_n)$$

The gains simply raise or lower the curve along the ordinates.

Now applying the Bresenham straight-line algorithm to f(a,y) provides a table consisting of the finally corrected 8-bit integrator voltage values at address locations 0-255 and the table is stored in RAM 46. The table for final compensation is represented by the nearly smooth curve 45 in FIG. 2.

Thus, no final compensation curve data has to be permanently stored. Only a small number, compared to the prior art and other alternatives, of basic compensation curves have to be stored and the memory capacity for storing the data for these curves is quite small since only a small number, possibly 20, coordinates are necessary to define a basic curve. The final or modified basic compensation curve is generated when the exposure factors are selected and even through this curve is defined by more coordinates only one relatively small memory block is needed to store the data for it.

It should now be clear that if the user or designer desires to include new components such as radiation sensors or image receptors or film/intensifying screen combinations to the AEC system or to exchange one type of any such components for another, it will only be necessary to determine the gain factor, G, for the component so it can be used in the gains multiplication equation set forth above but no change will have to be made in any basic compensation curve nor in the basic AEC circuit comprised of the integrator 32, RAM 46, DAC 55 and comparator 36 nor in any circuitry supplied from the output of said comparator.

To summarize operation, the final table is in RAM 46 before an exposure starts. Exposure is initiated by momentarily closing hand switch 49 in FIG. 1. The AEC control 39 sends out a command on line 50 to start the exposure. Simultaneously, counter 52 counts clock pulses and outputs their binary values as addresses to RAM 46 and these addresses correspond to exposure time increments extending over a critical period represented by 0 to 255 bytes on the abscissa of FIG. 2. If the time values of the bytes increase progressively in less than 100 microsecond steps, particularly about 80 microsecond steps in this example, the clock pulse frequency would have to be 20 ms ÷255 or about 100 kilohertz. The digitally represented compensating or reference voltages at each location are output from RAM 46 to DAC 55 which feed the resulting analog reference voltage signal to comparator input 37. Meanwhile the ramp or integrator output voltage is increasing as exemplified by either of the lines 33 or 34 in FIG. 2. When a ramp or integrator output voltage signal intersects, that is, equals the compensated reference signal as is the case at points 57 and 58 in FIG. 2, comparator 36 trips and sends out a signal on line 38 which is converted by the AEC control 39 to an exposure stop command signal.

Although an embodiment of the invention has been described in detail, such description is intended to be illustrative rather than limiting, for the invention may be variously embodied and is to be limited only by interpretation of the claims which follow.

I claim:

1. A diagnostic x-ray system having automatic exposure control means including comparator means responsive to a signal corresponding to integrated x-ray dosage related to image density comparing with a time-varying reference signal by providing a signal effective to terminate an x-ray exposure, means for storing digital values representative of the magnitudes of the reference signals over an incrementally increasing time range, a plot of said magnitudes versus time being designated a reference signal compensation curve, said system including x-ray tube means, collimator means adjustable to define the field of an x-ray beam projected from the source through a subject, radiation intensity sensor means, selectable x-ray image receptor means such as at least one of an image intensifier, a spot film device, a photospot camera and a radiographic film and intensifying screen combination, an x-ray tube power supply, conductors connecting the supply to said tube, and control means operative to couple and uncouple the supply and the tube to initiate and terminate exposures, and means for producing data for a final reference signal curve modified to compensate for the effect on image density resulting from the type of any of the radiation sensor, collimator adjustment, image receptor or choice of density that is used for the exposure, said last named means comprising:

means for storing a plurality of tables of digital values, respectively, representing a sequence of reference signal magnitudes and corresponding exposure termination times that resulted from producing the same integrator signal and, hence, images having a substantially constant density when materials having a range of x-ray attenuating properties were successively in said beam, the reference signal values corresponding to the y coordinates and the exposure termination times corresponding to the x coordinates of a plot of reference signal voltages versus exposure times, said tables thereby representing basic exposure time compensation curves having a predetermined number of coordinate pairs, said tables being formed when a particular kilovoltage (kV) or a limited range of kVs near said kV and a particular current (mA) or a limited range of mAs were applied to the x-ray for making the exposures to obtain the reference voltages, operator selection of kV and mA for making an x-ray exposure of a subject identifying the table to which the kV and mA combination relates, means for producing one or more gain factors representative of the type or condition of any of the radiation sensors, film/intensifying screen combinations and of the field size adjustment of the collimator and the image density desired by the user, that is to be used for making an x-ray exposure of the subject, processor means for multiplying the reference signal values in the identified basic compensation curve by the product of said gain factors to thereby define corresponding reference signal values of a corrected final compensation curve and for operating on the result with an algorithm that determines the coordinates for reference signal values and exposure times between succeeding pairs of x,y coordinates in the basic compensation curve to thereby yield a modified final compensation curve having a larger number of coordinate points and, hence, smaller increments of time between the reference signal values than in the basic curve, memory means for storing the resulting modified compensation curve having the increased numbers of reference signal values with respect to time, means for accessing from the memory means said modified reference signals sequentially in increasing order of their values at constant increments of time commencing with the start of the subject exposure, said comparator means being operative to compare the continually increasing accessed reference signal during the exposure with the increasing integrator signal and to respond to said signals attaining equality by producing a signal for causing deenergization of said x-ray tube and termination of the exposure.

2. The apparatus according to claim 1 wherein:
said modified reference signal values defining said final compensation curve are digital value stored, respectively, in said memory means at locations whose addresses increase correspondingly with time,
said means for accessing said modified reference signals comprising counter means having input means for a clock pulse train and responsive to counting clock pulses when said exposure is initiated to produce a series of addresses related to the number of counts corresponding to increments of time, said counter means having output means for supplying the addresses to said memory means for it to output said reference signal values in sequence.

3. The apparatus according to claim 2 wherein said time increments are 100 microseconds or less long.

4. The apparatus according to claim 2 wherein said addresses are represented by zero to 255 8-bit bytes each of which represents an equally increasing fraction of about 20 milliseconds of exposure time along the x axis of said modified final compensation curve and the full range of said integrator and reference signals in terms of volts are represented by zero to 255 8-bit bytes each of which represents an equally increasing fraction of the maximum voltage obtainable by said integrator.

5. The apparatus according to claim 2 wherein said addresses correspond to the successive x coordinates of the modified final compensation curve and the reference signal values at said 70 coordinates correspond to the y coordinates of said curve.

6. The apparatus in any of claims 1, 2, 3, 4 or 5 wherein said comparator means is an analog signal comparator having more than one input and said integrator signal is fed to one input,
a digital-to-analog converter for converting accessed digital reference signal values to corresponding analog reference signals, and
means coupling said analog reference signals to another input of said comparator means.

7. Automatic exposure control (AEC) means for use with a diagnostic x-ray system comprising an x-ray tube for projecting an x-ray beam to make an exposure, power supply means for energizing the tube including means for selecting tube current (mA) to be used for the exposure, and means for connecting the power supply means to the tube to apply a selectable kilovoltage (kV) between the anode and cathode of the tube during an exposure; conductors for connecting the power supply to the tube; and which system utilizes at least one of a radiation detector, a collimator, an image receptor such as an x-ray image intensifier, a radiographic film and intensifying screen combination, a spot film device and a photospot camera; and, including an integrating device for integrating a signal corresponding in magnitude to the image density and x-ray dosage delivered to a receptor during an exposure, means for comparing the integrated signal with a reference signal and responsive to comparison occurring by causing deenergization of the tube anode and termination of the exposure, said AEC means comprising:
means for storing a plurality of tables of digital values, respectively, representing successive reference signal magnitudes and corresponding exposure termination times that resulted from producing the same integrated signal and, hence, images having a substantially constant desired density when materials having a range of x-ray attenuating properties were successively in said beam, each of said tables being formed when a particular kV or limited range of kVs and an mA value or limited range of mA values were energizing the tube to obtain the reference signal magnitudes and corresponding exposure times while said materials were in the beam, said tables thereby representing basic exposure time compensation curves, operator selection of the kV and mA at which it is desired to make an x-ray exposure of the anatomy resulting in calling up the table to which the selected kV and mA relates, means for producing gain factors corresponding, respectively, to any of the radiation sensors, film/intensifying screen combinations chosen to be used during the exposure and to the field size adjustment of said collimator and to the image density desired by the operator, processor means for multiplying said reference signal values for the identified basic compensation curve by the product of said gain factors to provide reference signal values corresponding in time, respectively, with the time in the basic compensation curve to thereby define the data for a corrected final compensation curve and for operating on the result with an algorithm that finds values of the reference signal and corresponding exposure times lying between said values in the basic compensation curve to thereby provide data for making a table for a final corrected compensation curve wherein the signals corresponding to the reference signals in the basic curve are then reference signals corresponding respectively with exposure times, memory means for storing the reference signal values, means for accessing said reference signals sequentially in increasing value order at the end of constant increments of time commencing when the exposure is initiated, said comparator means being operative to compare continuously the increasing reference signal produced during an exposure with the reference signals accessed during the exposure and to respond to the integrator signal attaining equality with the reference signal by producing a signal for deenergizing the x-ray tube and terminating the exposure at the time equality is attained.

8. The apparatus according to claim 7 wherein:
said reference signal values are stored in said memory means at addressable locations,
said means for accessing said signals comprises counter means having input means for a clock pulse sequence defining said time increments and output means for signals constituting addresses to said memory means, said counter means producing the address correspondingly with the clock pulses for said accessing of the reference signal values in sequence.

9. The apparatus according to any of claims 7 or 8 wherein said increments of time are 100 microseconds or less long.

10. A method of automatically controlling the duration of x-ray exposures of anatomy to obtain x-ray images having a desired density in a diagnostic x-ray system wherein an exposure is terminated by deactivating an x-ray tube in response to a comparison being made with a comparator between an integrated signal that increases in magnitude with time in proportion to x-ray dose emergent from the anatomy and reference signal defining a compensation curve that changes in amplitude with time, the method comprising the steps of:

storing a plurality of data sets defining the coordinates of a relatively small number of points on a plurality of basic compensation curves representing reference signal magnitudes versus increments of x-ray exposure time corresponding to integrated signal magnitudes at which said comparison is made and an exposure is to be terminated for obtaining said desired image density, each of the data sets defining said curves relating to a kilovoltage (kV) or a limited range of kVs and a current (mA) or a limited range of mAs applied to said x-ray tube, developing gain factors representative of any one or all of the type or operating characteristic of the radiation sensor, image receptor, film and intensifying screen combinations and chosen density that will be in effect during making the x-ray exposure at a user selected kV and mA, multiplying the respective basic compensation curve signal magnitudes by said gain factors and processing the signals with an algorithm that results in additional coordinate points equally spaced from each other in respect to time being determined between said relatively small number of points to thereby produce the coordinates for reference signals versus relatively smaller increments of exposure time representing a modified compensation curve, storing said reference signals in a memory device at addresses corresponding to the exposure times to which they relate before said exposure is initiated and concurrently with initiating the exposure addressing said reference signals at a rate that results in supplying them from said memory device to said comparator at the time to which they relate, and simultaneously supplying said integrator signal representing increasing integrated x-ray dose relative to time to said comparator for said comparator to produce a signal that is effective to terminate said exposure when the reference signal and integrator signal compare.

* * * * *